(12) United States Patent
Rose

(10) Patent No.: US 9,545,286 B2
(45) Date of Patent: Jan. 17, 2017

(54) THERMOTHERAPY APPLICATION AND CONTROL SYSTEM

(71) Applicant: Physiolab Technologies Limited, Colchester, Essex (GB)

(72) Inventor: Nicholas James Rose, London (GB)

(73) Assignee: Medicold Limited (GB)

( * ) Notice: Subject to any disclaimer, the term of this patent is extended or adjusted under 35 U.S.C. 154(b) by 0 days.

(21) Appl. No.: 14/297,202

(22) Filed: Jun. 5, 2014

(65) Prior Publication Data

US 2014/0371732 A1      Dec. 18, 2014

Related U.S. Application Data

(63) Continuation of application No. 12/253,521, filed on Oct. 17, 2008, now abandoned.

(51) Int. Cl.
*A61F 7/00* (2006.01)
*A61B 18/02* (2006.01)
(Continued)

(52) U.S. Cl.
CPC ............... *A61B 18/02* (2013.01); *A61F 7/10* (2013.01); *F28F 13/10* (2013.01);
(Continued)

(58) Field of Classification Search
CPC .... A61N 7/02; A61N 1/00; A61B 2018/0281; F28F 13/10; C10M 171/001; A61C 15/041; A61C 19/066; A61K 8/042; A61K 8/817; A61K 8/8176; A61Q 19/00; A61Q 5/06; A61F 7/007
(Continued)

(56) References Cited

U.S. PATENT DOCUMENTS 3,080,723 A  3/1963  Price
4,362,165 A  12/1982  Carmon et al.
(Continued)

FOREIGN PATENT DOCUMENTS

EP   1929980 A1   6/2008
EP   1977709 A1   10/2008
(Continued)

OTHER PUBLICATIONS

"PCT International Search Report dated Apr. 1, 2010 for PCT/GB2009/002497," 5 pgs.
(Continued)

*Primary Examiner* — Scott Medway
(74) *Attorney, Agent, or Firm* — Craig A. Fieschko, Esq.; DeWitt Ross & Stevens S.C.

(57) ABSTRACT

Apparatus for applying thermotherapy to a part of the human or animal body comprising an applicator having a flexible enclosure in which thermal energy transfer fluid can circulate, a connector for connecting the applicator to a control system, an interface layer for providing a thermally conductive interface between the flexible enclosure and a treatment site and, an electrically conductive supporting layer for supporting the interface layer and capable of being energized by an electrical signal from the control system to improve the thermal conductivity of the interface layer. The apparatus also includes a valve unit for connecting the applicator to a control system, a heat exchanger for cooling a thermal energy transfer fluid and a control system for controlling the application of thermotherapy. The apparatus permits manipulation and control of the molecules of the interface layer and a thermal energy transfer fluid to improve the thermal energy transfer efficiency between the applicator and a treatment site.

29 Claims, 15 Drawing Sheets

(51) Int. Cl.
*A61F 7/10* (2006.01)
*F28F 13/10* (2006.01)
*A61F 7/02* (2006.01)

(52) U.S. Cl.
CPC .............. *A61B 2018/0243* (2013.01); *A61B 2018/0281* (2013.01); *A61F 2007/0056* (2013.01); *A61F 2007/0076* (2013.01); *A61F 2007/0078* (2013.01); *A61F 2007/0247* (2013.01)

(58) Field of Classification Search
USPC .......... 607/96; 604/294; 602/2; 205/414, 87
See application file for complete search history.

(56) References Cited

U.S. PATENT DOCUMENTS

| | | | |
|---|---|---|---|
| 4,664,118 A | 5/1987 | Batters | |
| 4,997,425 A | 3/1991 | Shioya et al. | |
| 5,002,336 A | 3/1991 | Feher | |
| 5,038,779 A | 8/1991 | Barry et al. | |
| 5,129,391 A | 7/1992 | Brodsky et al. | |
| 5,662,624 A | 9/1997 | Sundstrom et al. | |
| 5,741,579 A | 4/1998 | Nishizawa | |
| 5,758,505 A * | 6/1998 | Dobak et al. | 62/6 |
| 5,766,236 A | 6/1998 | Detty et al. | |
| 5,800,490 A | 9/1998 | Patz et al. | |
| 5,817,145 A | 10/1998 | Augustine et al. | |
| 5,879,378 A | 3/1999 | Usui | |
| 5,944,685 A | 8/1999 | Muroki | |
| 6,071,304 A | 6/2000 | Augustine et al. | |
| 6,416,534 B1 | 7/2002 | Montagnino et al. | |
| 6,475,307 B1 | 11/2002 | Nystrom et al. | |
| 6,585,670 B2 | 7/2003 | Augustine et al. | |
| 6,685,681 B2 | 2/2004 | Lockwood et al. | |
| 6,691,355 B1 | 2/2004 | Liu | |
| 6,794,030 B1 | 9/2004 | Okada et al. | |
| 6,800,074 B2 | 10/2004 | Henley et al. | |
| 6,927,316 B1 | 8/2005 | Faries et al. | |
| 7,195,624 B2 | 3/2007 | Lockwood et al. | |
| 7,678,716 B2 | 3/2010 | Yahiaoui et al. | |
| 7,744,640 B1 | 6/2010 | Faries et al. | |
| 7,822,488 B2 | 10/2010 | Jonsen et al. | |
| 7,968,117 B1 | 6/2011 | Morrison et al. | |
| 2001/0039391 A1 | 11/2001 | Augustine | |
| 2002/0193849 A1 * | 12/2002 | Fenn et al. | 607/89 |
| 2004/0210254 A1 | 10/2004 | Burnett et al. | |
| 2005/0061681 A1 | 3/2005 | Lim et al. | |
| 2006/0191675 A1 | 8/2006 | Fletcher et al. | |
| 2007/0016270 A1 | 1/2007 | Stelea et al. | |
| 2007/0282282 A1 | 12/2007 | Wong, Jr. et al. | |
| 2010/0217349 A1 | 8/2010 | Fahey | |
| 2013/0283841 A1 * | 10/2013 | Markowitz et al. | 62/296 |

FOREIGN PATENT DOCUMENTS

| | | | |
|---|---|---|---|
| GB | 2283678 A * | 5/1995 | ............. A61B 17/36 |
| GB | 2418614 A | 5/2006 | |
| JP | 2004350990 A * | 12/2004 | ............... A47G 9/10 |
| WO | 9504508 A1 | 2/1995 | |
| WO | 9522949 A1 | 8/1995 | |
| WO | 0040185 A1 | 7/2000 | |
| WO | 2005044141 A2 | 5/2005 | |
| WO | 2008141047 A1 | 11/2008 | |

OTHER PUBLICATIONS

"PCT Written Opinion dated Apr. 1, 2010 for PCT/GB2009/002497," 3 pgs.
"Search Report dated Jan. 31, 2006 for GB 0416879.5," 1 pg.
"Search Report dated Feb. 4, 2009 for GB 0819098.5," 3 pgs.

* cited by examiner

SECTION B-B'

THERMOTHERAPY APPLICATION AND CONTROL SYSTEM

CROSS REFERENCE TO RELATED APPLICATION

This application is a continuation application of U.S. patent application Ser. No. 12/253,521, filed Oct. 17, 2008 and titled "THERMOTHERAPY APPLICATION AND CONTROL SYSTEM," the entire content of which is incorporated herein by reference.

FIELD OF THE INVENTION

The invention relates to an improved thermotherapy application and control system for applying thermotherapy to parts of the human or animal body to reduce, increase or maintain the body temperature at a treatment site.

BACKGROUND

It is known that reducing the temperature of a part of the human or animal body by the application of Cryotherapy following injury and/or surgery reduces swelling and pain and expedites healing. Likewise, the maintenance of a constant temperature during surgery is extremely important to reduce internal bleeding, bruising and swelling. Cryotherapy is also known to be beneficial as part of a sports training program when applied before and after sporting events and periods of intense physical activity.

Studies have shown that the optimum benefit to be gained by cooling and maintaining the body temperature is achieved by reducing the temperature in the affected area as soon as possible after the injury has occurred or surgery has commenced. Studies have also shown that simply applying excessively low temperatures to the target area does not achieve the optimum cooling effect and can be harmful to the patient as it can cause the onset of cold burn or frostbite.

Known methods for effecting localized temperature reduction of various parts of the human body require the use of cumbersome cooling pads, ice packs, frozen gels and the like. A problem of such methods of quickly reducing the body temperature is that the rate at which they reduce the body temperature is slow. A further problem is that due to this slow rate of body temperature reduction, there is a tendency for excessively low temperatures to be applied to the injury site in an attempt to achieve a more rapid rate of temperature reduction and make the treatment more effective. A further problem is that when ice packs and the like are placed on an injury site, the ice begins to melt and provide a constantly changing and uncontrollable temperature.

It is known that the principle cause of the delay and ineffectiveness of the heat transfer is due to the extremely small 'real' area of contact at the microscopic level between the applicator and the treatment site. Studies have shown that the 'real' area of contact is less than around 5% of the total area over which optimum heat transfer could occur, the remainder of the area being made up of air gaps. The concentration of the flow of heat at the points of contact creates 'hot spots' which increase the localized temperature and melt the surrounding ice or gel pack.

The applicant has appreciated that the full potential benefits of Cryotherapy are not being exploited by the known apparatuses for the fast application of cooling.

The applicant has also appreciated that to improve the efficiency of heat transfer between an applicator and the treatment site, there is a need for an improved interface between the applicator and treatment site that closely conforms to the contours of the area of a patient's body undergoing treatment in order to maximize the real contact area between the applicator and treatment site. The inventor has also previously appreciated that the thermal conductivity of the interface must be high and barriers to heat transfer minimized in order to optimize the efficiency of heat transfer and thereby permit the maximum cooling effect to be applied in the shortest space of time.

United Kingdom patent application no. GB0416879.5 describes a device addressing these concerns.

SUMMARY OF THE INVENTION

The invention in a first aspect provides an applicator for applying thermotherapy to a part of the human or animal body as defined in claim 1 to which reference should now be made.

The invention in a second aspect provides a valve unit for connecting an applicator for applying thermotherapy to a part of the human or animal body to a control system as defined in independent claim 21 to which reference should now be made.

The invention in a third aspect provides a heat exchanger for varying the thermal energy of a thermal energy transfer fluid to be circulated through an applicator for applying thermotherapy to a part of the human or animal body as defined in claim 25 to which reference should now be made.

The invention in a fourth aspect provides a control system for controlling an applicator for applying thermotherapy to a part of the human or animal body as defined in independent claim 27 to which reference should now be made.

Preferred features of the various aspects of the invention in its various aspects are set out in the dependent claims to which reference should also now be made.

The invention in a first aspect provides an improved applicator for applying thermotherapy which has an electrically conductive supporting layer for supporting the interface layer, and for receiving and electrical signal from a control system. This enables the supporting layer to be energized by an electric current from a control system. This is advantageous because the molecules of the interface material can be excited in order to enhance molecular contact between the interface layer and a patient's skin and increase the thermal conductivity of the interface layer.

Preferably, the electrically conductive supporting layer is positioned within the interface layer so that when the supporting layer is energized by a control system, the molecules of the interface layer on either side of the supporting layer are easily and effectively excited.

Preferably a primary, measurement circuit connects the electrically conductive supporting layer and a connector for connecting the applicator to a control system to facilitate the transfer of data, for example temperature data, from sensors positioned at the interface to the control system. Preferably a secondary, driving circuit connects the supporting layer to the connector so that an electric current may be easily be passed directly to the electrically conductive supporting layer from the control system.

Preferably an intermediate layer having a plurality of holes and/or a network of flow tubes is provided in the enclosure to provide a complex flow path for thermal energy transfer fluid to create turbulent fluid flow to enhance the thermal transfer characteristics of the transfer fluid and to distribute the fluid.

The invention in a second aspect provides a valve unit for an applicator for applying thermotherapy which imparts movement to thermal energy transfer fluid in an enclosure of the applicator. The agitator is beneficial because it agitates the fluid to induce turbulent flow and therefore enhances the thermal energy transfer characteristics of the fluid.

The invention in a third aspect provides a heat exchanger for use with an applicator for applying thermotherapy, having an improved heat sink with a plurality of irregularly positioned and/or irregularly shaped projections which extend into a flow path for the thermal energy transfer fluid to disturb the flow the fluid and create turbulent, non-laminar fluid flow. This is advantageous because the turbulent fluid flow enhances the thermal energy transfer characteristics of the fluid making it more efficient at exchanging thermal energy with a thermal energy source coupled to the heat sink.

The invention in a fourth aspect provides a controller for controlling an applicator for applying thermotherapy, having an electrical current source for energizing the electrically responsive supporting layer of the applicator and a controller for controlling the properties of current flowing from the current source. This is particularly advantageous as it provides for accurate control of the behavior of an interface material between the applicator and a treatment area which enhances the thermal energy transfer efficiency between the applicator and the treatment site.

BRIEF DESCRIPTION OF THE FIGURES

A preferred embodiment of the invention will now be described, by way of example, with reference to the attached figures in which:

FIG. 15b is an enlarged cross-section through line A-A' of FIG. 15a;

FIG. 15c is an enlarged cross-section through B-B' of FIG. 15a;

DETAILED DESCRIPTION

For the avoidance of doubt, where the following description of the preferred embodiments of the present invention refers to the application of Cryotherapy or cooling to reduce the temperature of a part of the human body and/or maintain the reduced body temperature, it should be noted that the system can also be used for the application of thermal energy to increase the temperature of a part of the human body and/or to maintain an elevated body temperature. The system can also be used to selectively apply thermal energy to vary the temperature of a part of the body and to maintain it at the desired temperature.

Furthermore, where the following description refers to the application of cooling to a part of the body or a patient's treatment site this is also intended to cover a part of the animal body and a treatment site on an animal.

Where "thermal energy" is referred to in the following description, it means that the thermal or kinetic energy being at a lower temperature than the body tissue at the treatment area.

It is known that the thermal conductivity of the materials used to provide the interface between a thermotherapy applicator and a treatment site on the body has a significant effect on the efficiency of thermal energy transfer between the treatment site and a thermal energy source. Factors that are known to affect the efficiency of the thermal energy transfer process are: i) how efficiently thermal energy is transferred away from the applicator; ii) how efficiently thermal energy is released from a thermal energy transfer medium to a heat exchanger; iii) how easily the thermal energy can be released from the heat exchanger, i.e. how easily thermal energy is dissipated to a heat sink; (iv) the thermal impedance of the applicator; and (v) the 'real' area of physical contact between the applicator and the treatment site. These factors are addressed by the preferred embodiments of the present invention as described below.

Figure 1:
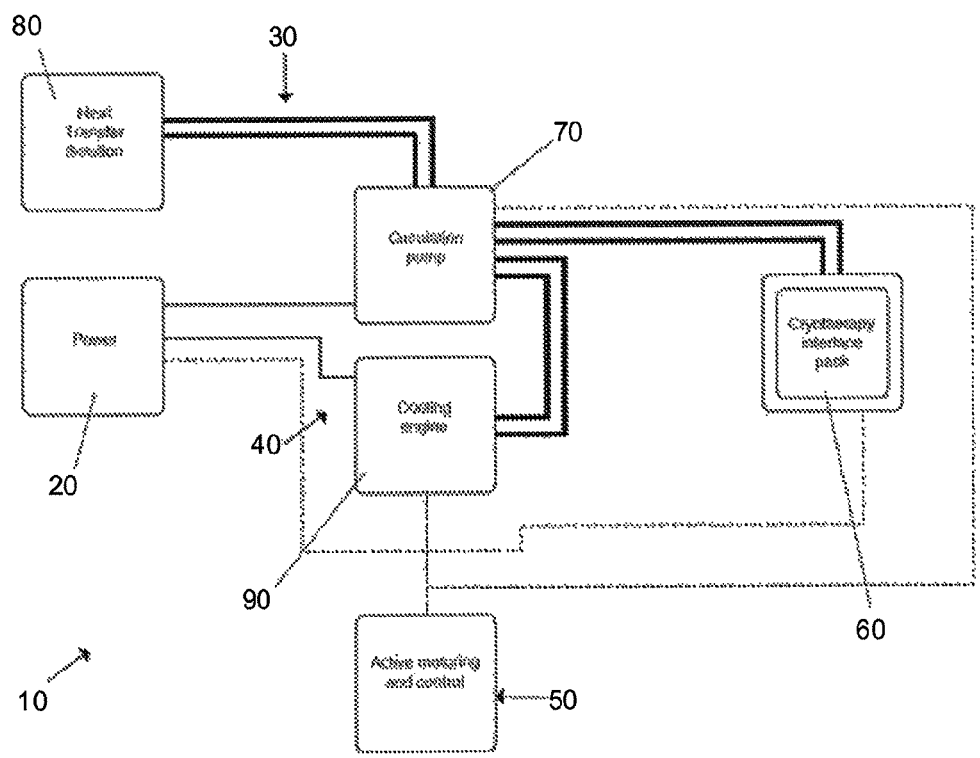
FIG. 1 is a schematic illustration of a system for the application of thermotherapy embodying the present invention.

As shown in FIG. 1, a thermotherapy system 10 for controlling the temperature of a part of the body includes a power source 20 for supplying power to the system, a thermal energy transfer fluid recirculation system 30 for circulating thermal energy transfer fluid, a cooling system 40 for cooling the thermal energy transfer fluid, a monitoring and control system 50 for monitoring and controlling the various components of thermotherapy system 10 and an applicator 60 for applying thermal energy to a part of the body.

Power source 20 may be one of a number of types of power sources known to the skilled person and shall not therefore be described in detail. A fuel cell is particularly suitable for powering the components of thermotherapy system 10.

Thermal energy transfer fluid recirculation system 30 includes a pump 70 which may be one of a number of types of pump that are known to the skilled person and shall not therefore be further described. Recirculation system 30 also includes a reservoir 80 for storing a supply of thermal energy transfer fluid. Pump 70 pumps thermal energy transfer fluid from reservoir 80 through cooling system 40 and applicator 60 before returning it to reservoir 80.

The thermal energy transfer fluid is preferably a non-aqueous fluorinert fluid which can be cooled more quickly than water and retains thermal energy for longer than water and therefore provides for more efficient transfer of thermal energy from cooling system 40 to applicator 60. Preferably the thermal energy transfer fluid remains in a fluid state at least in the temperature range of −20° C. to +30° C.

Figure 2:
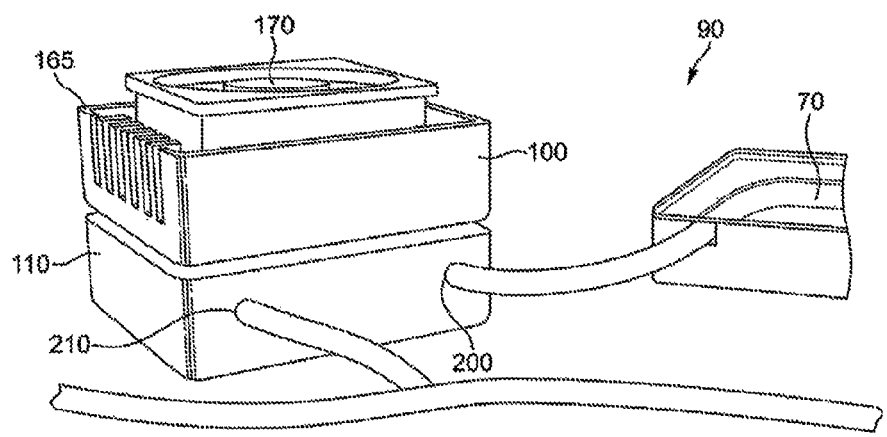
FIG. 2 is a top perspective view of the cooling source of FIG. 1 for cooling a thermal energy transfer fluid.
Figure 3:
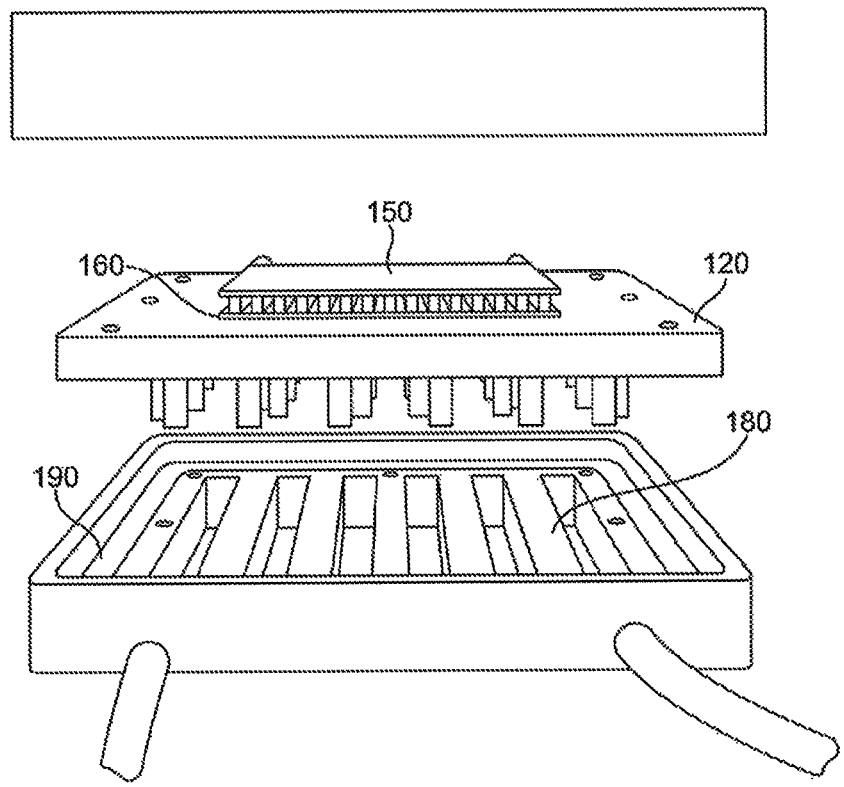
FIG. 3 is an exploded view of the cooling source of FIG. 2.
Figure 4:
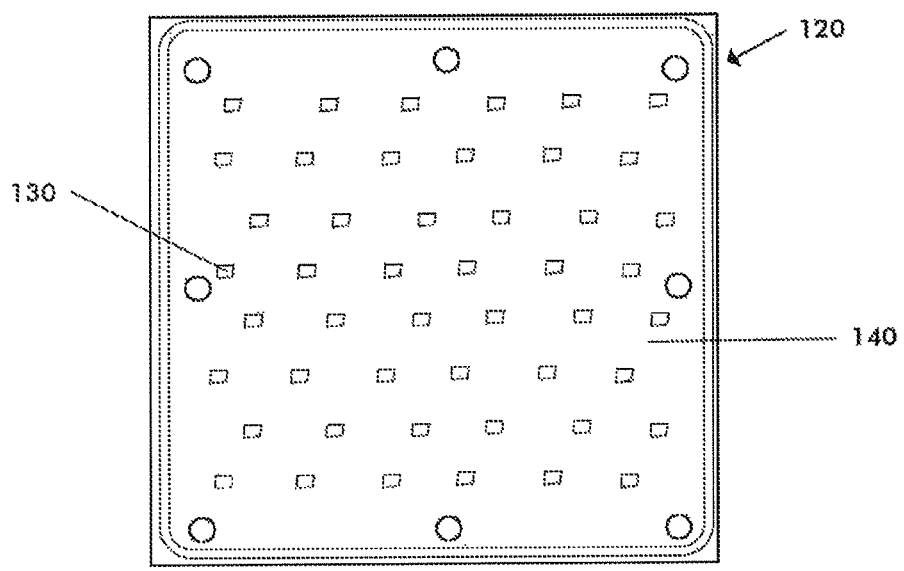
FIG. 4 is a bottom view of a heat sink of the cooling source of FIGS. 2 and 3.

Cooling system 40 includes a cooling source 90 shown in detail in FIGS. 2 and 3. Cooling source 90 includes a casing having upper and lower casing sections 100 and 110. Between casing sections 100 and 110 is heat sink 120 shown in more detail in FIG. 4. Heat sink 120 has a plurality of projections 130 that project from a plate 140. Projections 130 are generally in an ordered, matrix formation but at least some are irregularly shaped and/or at least some are positioned irregularly relative to other projections, so that some of projections 130 are out of alignment with the generally ordered, matrix configuration.

As upper and lower casing sections 100 and 110 are closed together around heat sink 120, projections 130 of heat sink 120 are received within channels 180 in lower casing section 110. A seal 190 is provided between lower casing section 110 and heat sink 120 to prevent fluid escaping where upper and lower casing sections 100,110 join. Channels 180 are arranged in lower casing section 110 to provide a continuous flow path for fluid between a cooling source inlet 200 and an outlet 210.

Thermal energy transfer fluid passing along the flow path is forced to flow around projections 130 and the irregular shape and/or irregular positions of projections 130 induces turbulent, non-laminar flow of the thermal energy transfer fluid and increases the rate of thermal energy transfer from the thermal energy transfer fluid to the heat sink 120.

Preferably, cooling source 90 operates on the principle of thermoelectric cooling and therefore includes a pair of plates 150,160 connected to a transistor. When a potential difference is applied by power source 20 across the transistor, the temperature of the upper plate 150 increases and the temperature of lower plate 160 decreases. The thermal energy generated at plate 160 is transferred by conduction through heat sink 120 to projections 130 to cool the fluid. Fins 165 are provided on upper casing section 100, increasing the surface area exposed to the surrounding air and allowing the flow of air to carry thermal energy away from cooling source 90. A cooling fan 170 is also provided in a top surface of upper casing section 100, preferably amongst fins 165 to provide additional air movement and cooling of plates 150,160 and heat sink 120.

By reversing the polarity across the transistor, the temperature of the upper plate 150 decreases and the temperature of lower plate 160 increases so that the thermal energy generated at plate 160 is transferred by conduction through heat sink 120 to projections 130 to heat the fluid.

Figure 5:
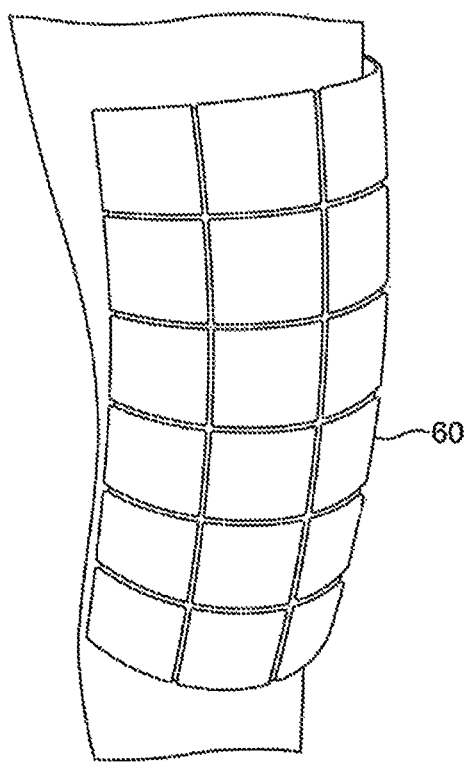
FIG. 5 shows an example of the applicator of FIG. 1 in position on a patient's knee.
Figure 6:
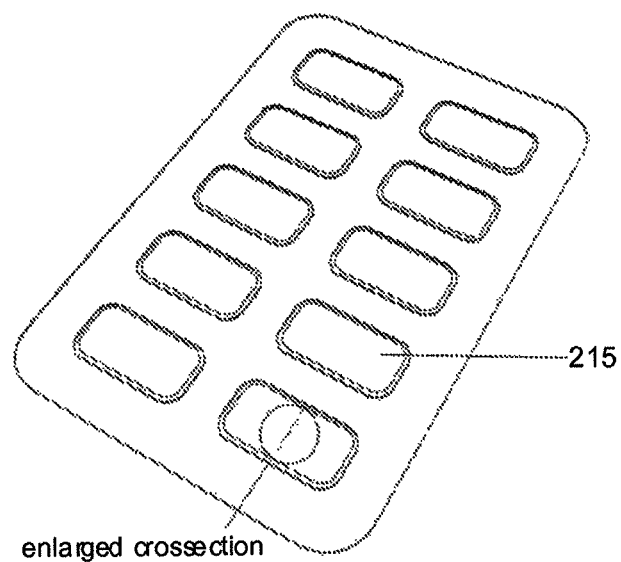
FIG. 6 is a top perspective view of the applicator of FIG. 5.
Figure 7:
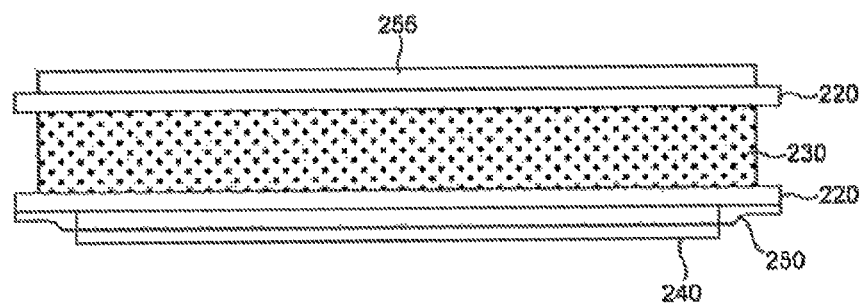
FIG. 7 is an enlarged cross-section through a discrete heat transfer portion of the applicator of FIG. 6.

As shown in FIG. 5, applicator 60 may be positioned on a part of the patient's body to apply thermal energy from cooling source 90 to the patient. Applicator 60 may also be shaped to confirm to a particular body part. In one embodiment shown in FIG. 6, applicator 60 is made up of a number a number of discrete thermal energy transfer portions 215, one of which is shown in cross-section in FIG. 7.

In its simplest form, applicator 60 consists of a bladder-like pouch made from a pair of polyester membranes 220. Preferably these are approximately 12 microns thick and composed of PolyEthylene Tetrapthalate. Membranes 220 define a chamber 230 in which thermal energy transfer fluid can be circulated under pressure by pump 70. Applicator 60 has thermal energy transfer fluid inlet and outlet tubes (not shown) for circulating thermal energy transfer fluid through chamber 230. The tubes are attached to applicator 60 by snap-fit type connectors containing valves, or other quick-release type valve fittings. This allows applicators 60 of different shapes and sizes that conform to the general shape of the particular body part being treated to be quickly and easily connected to cooling system 40.

Figure 8:
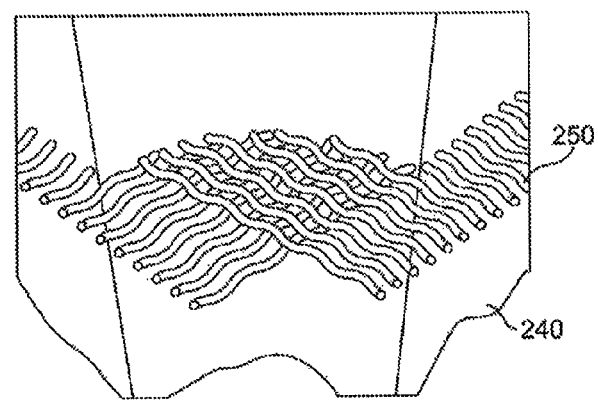
FIG. 8 is an enlarged image of a composite interface layer of the applicator of FIGS. 6 and 7 with a supporting layer positioned within the interface layer.

An interface layer 240 of flexible, gel-like material is provided on a surface of applicator 60 for contacting the patient's skin. The width of interface layer 240 is preferably, but not limited to, between 1.5 mm and 5 mm thick. As shown in FIG. 8, a supporting mesh layer 250 is provided to support gel-like interface layer 240. Preferably, supporting layer 250 is positioned through interface layer 240. The mesh layer may be an open or close weave and will be discussed in more detail later. A portion of the supporting layer 250 protrudes from interface layer 240 and is bonded or otherwise joined to one of membranes 220 around an edge portion of the supporting layer surrounding interface layer 240 to retain interface layer 240 against a surface of applicator 60.

Figure 9:
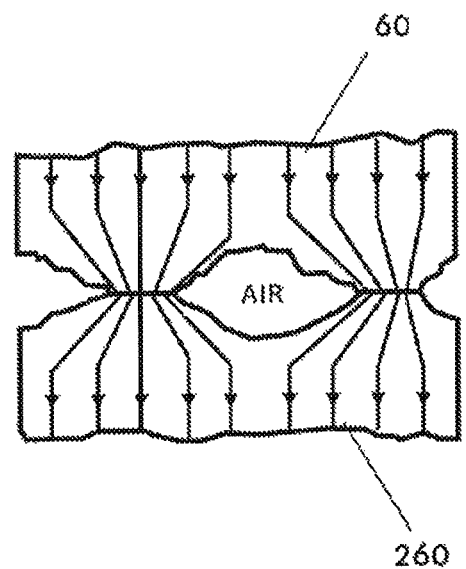
FIG. 9 is an enlarged illustration of the air gaps that exist at the interface between the patient's skin and known applicators of thermal energy.
Figure 10:
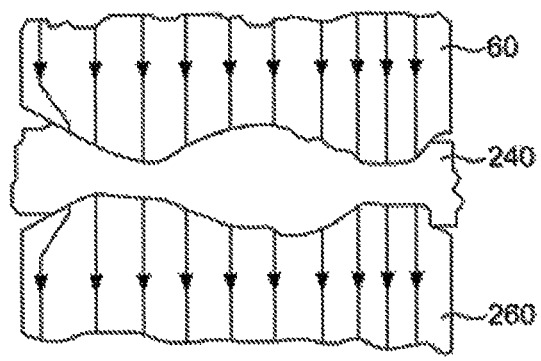
FIG. 10 is an enlarged illustration of the interface between the patient's skin and an applicator with an attached composite interface layer embodying the present invention.

As shown in FIG. 9, in the absence of an interface layer 240, air gaps exist between applicator 60 and the patient's skin 260. Air gaps provide a barrier to effective thermal energy transfer and lead to a concentration of thermal energy transfer or 'hot spots' at the areas of contact which heat up the surrounding thermal energy transfer fluid. As shown by the pattern of arrows in FIG. 10, specially formulated composite interface layer 240 works at the microscopic level to fill the air gaps, thereby reducing barriers to the flow of thermal energy energy and optimising the transfer of thermal energy between applicator 60 and the patient's skin 260. Tests by the inventor have shown that interface layer 240 is capable of increasing the surface contact at the microscopic level by up to twenty times that of known ice or gel packs.

The applicant has appreciated that solid bonds between particles provide optimum thermal conductivity of interface layer 240 while flexible bonds between particles provide optimum conformability of the interface layer to the patient's skin. Based on these principles, the inventor has developed a gel-like material that can be considered to be a visco-elastic solid but which has a fluid-like, tacky, yet dry surface. This gives the material a unique and exceptional ability to conform to, and make contact with, the surface of the body at the microscopic level, while simultaneously providing a highly thermally efficient interface between the applicator 60 and the patient's skin.

Interface layer 240 generally consists of a composite material having a cross-linked silicone formulation that is loaded with highly conductive particles, preferably microparticles. The particles are preferably ceramic and can be one or a combination of Aluminium Oxide, Boron Nitride, Silver plated Copper and Amorphous Carbon. However, conductive particles of other materials may be used alone or in combination with particles of other materials to provide variation in the thermal energy transfer characteristics. The specific properties of interface material 240 may be controlled by varying the choice of gel-like material, the highly conductive particles embedded within the gel and the weave characteristics and material of supporting layer 250.

In a preferred composition, the interface layer is a Silicon based gel loaded with particles of Boron Nitride. Preferably the ratio of Silicon based gel to Born Nitride particles is in the range 0.5 to 0.8 Silicon to the range of 0.5 to 0.2 Boron Nitride. More preferably, the ration of Silicon based gel to Boron Nitride particles is 0.6 to 0.7 Silicon to the range of 0.4 to 0.3 Boron Nitride.

Figure 11:
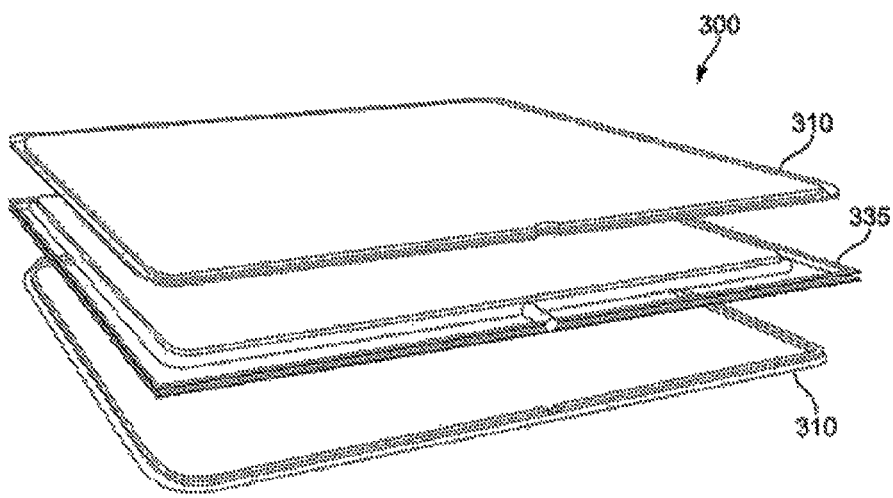
FIG. 11 is an exploded view of a discrete thermal energy transfer portion of the applicator of FIG. 5.
Figure 12:
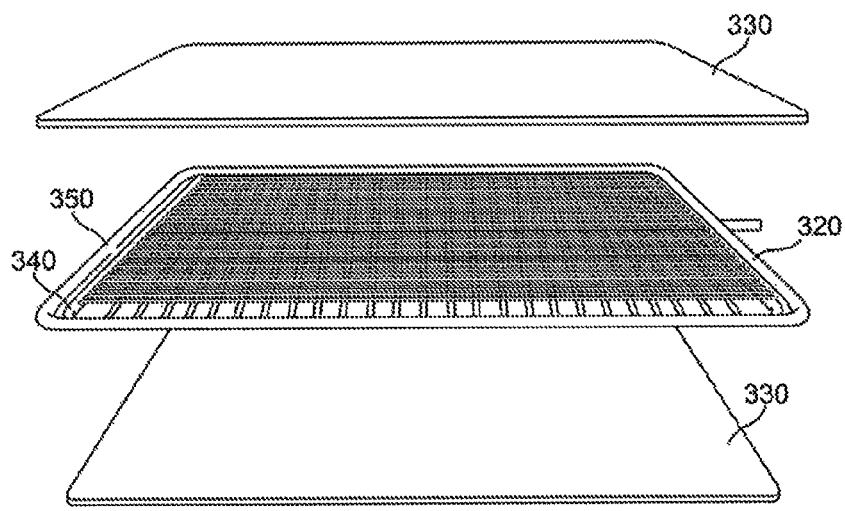
FIG. 12 is a further exploded view of a discrete thermal energy transfer portion of the applicator of FIGS. 5 and 11.

FIGS. 11 and 12 are exploded views of one a number of discrete thermal energy transfer portions 300 according to an alternative embodiment of applicator 60. Each thermal energy transfer portion 300 is defined by a bladder-like pouch made from a pair of polyester membranes 310 defining a chamber for thermal energy transfer fluid. Within the chamber is a plurality of flow tubes 320 for carrying thermal energy transfer fluid sandwiched between a pair of gel-like interface layers 330 made from the same material as that described above with reference to FIGS. 7 to 10.

A thermal energy transfer fluid distribution circuit includes flow pipes 335 that pass between thermal energy transfer portions 300 and deliver thermal energy transfer fluid to an inlet of each transfer portion 300. A cold 340 and a hot 350 thermal energy transfer fluid circuit pass around an internal perimeter of the chamber defined by membranes 310 and are in fluid communication with each other via the network of flow tubes 320. Flow tubes 320 permit relatively colder thermal energy transfer fluid flowing under pressure from reservoir 80 and entering cold fluid circuit 340 at the inlet of each discrete portion 300 to flow across from one side of thermal energy transfer portion to the other and into hot thermal energy transfer fluid circuit 350. The thermal energy transfer fluid then flows out from an exit of each discrete portion 300 into flow pipes 335 and is returned to reservoir 80.

The plurality of flow tubes 320 distribute thermal energy transfer fluid across as large an area of the chamber as possible and preferably across substantially the entire area of the chamber of each thermal energy transfer portion 300 so that the transfer of thermal energy between the thermal energy transfer fluid and a treatment site occurs evenly over each thermal energy transfer portion 300. However, by varying the number and pattern of flow tubes 320 over each discrete portion 300 and/or by varying the number and pattern of flow tubes from one discrete portion 300 to the next, the thermal energy transfer properties of applicator 60 can be controlled such that cooling is applied at different rates across the contact area between applicator 60 and the treatment site.

One or more means for constricting the applicator 60 may be provided to induce applicator 60 to adopt a certain shape and conform more closely to the shape of the particular body part being treated. In one embodiment, the pattern of the weave of mesh layer 250 may be varied across different parts of applicator 60 to form a shape that more closely conforms to a part of the body, such as for example a tube for surrounding a patient's arm or leg.

Elastic straps, bands or tubes, a wrap or band of Nylex® material or thin straps of a hook and loop fastener such as Velcro® may alternatively, or additionally be provided to shape and constrict applicator 60 around the part of the body to which thermotherapy is to be applied. In another embodiment, one or more air pockets 255 (see FIG. 7) or channels is or are provided on the opposite side of applicator 60 to interface layer 240 so that air pressure may be applied through the pocket to urge applicator 60 and attached interface layer 240 into contact with the treatment site.

In a further alternative, a dielectric elastomer is suspended within a pocket 255 filled with fluid on the opposite side of applicator 60 to interface layer 240. When the elastomer is activated by an applied electrical current, the volume of the envelope available to the fluid is reduced hence the fluid exerts outward pressure causing the pouch to conform more effectively to the body surface under treatment.

Returning to FIG. 1, the monitoring and control system 50 is powered by power supply 20 and is connected to applicator 60, pump 70 and cooling source 90. Monitoring and control system 50 receives temperature data from thermistors positioned at the treatment site and allows adjustments to be made to the temperature at the treatment site as will described further below.

Figure 13:
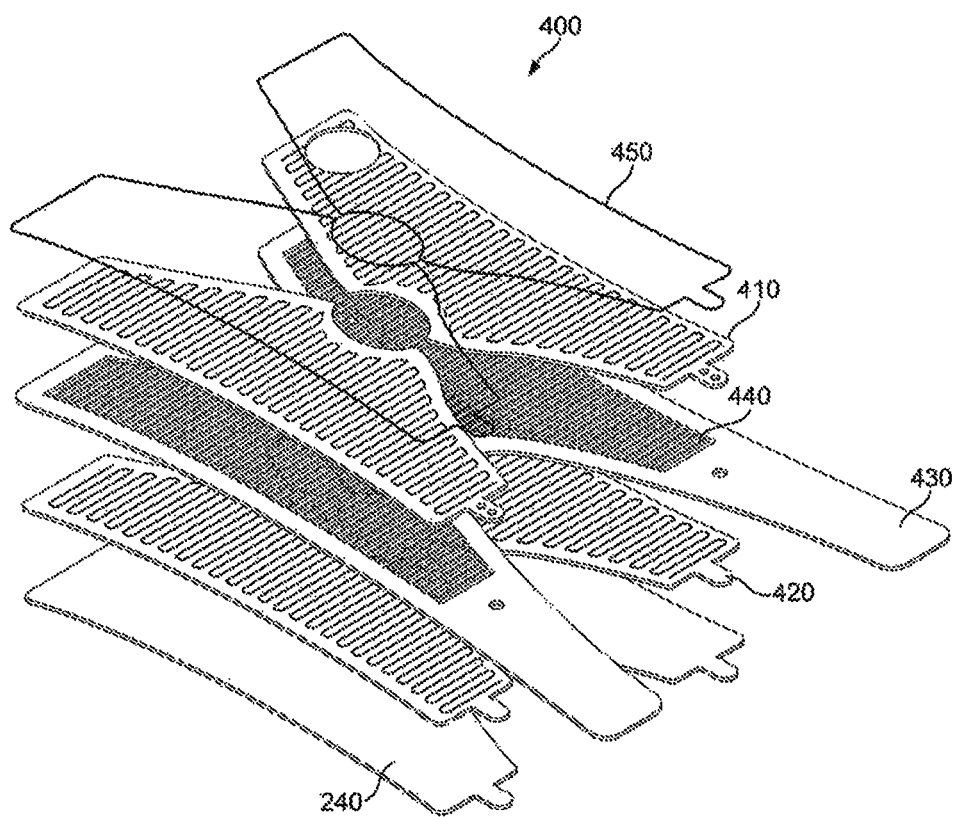
FIG. 13 is an exploded view of a knee applicator embodying the present invention.

An example of a preferred construction of an applicator 400 for use on a patient's knee is shown in FIG. 13. Knee applicator 400 is constructed from a number of layers. A cold layer 410 and a hot layer 420 are positioned on opposite sides of an intermediate layer 430. The intermediate layer has a plurality of holes 440 that are shown by way of example in FIGS. 13 and 14 as rectangular slots. The pattern and shape of holes 440 is not intended to be limited to slots, and other hole shapes and locations could also be used, for example, circular holes or cut-outs.

Cold and hot layers 410 and 420 are joined around their perimeter to opposite sides of intermediate layer 430 by, for example a line of weld or other suitable join 450 to form a sealed pouch either side of a central knee hole. When the applicator is fitted, the knee hole fits over the patient's knee and the sealed pouches contact the sides of the knee. A gel-like interface layer 240 with supporting mesh layer 250 is welded or otherwise attached to an outside surface of hot layer 420 for providing an interface between the applicator and the patient's knee.

Figure 14:
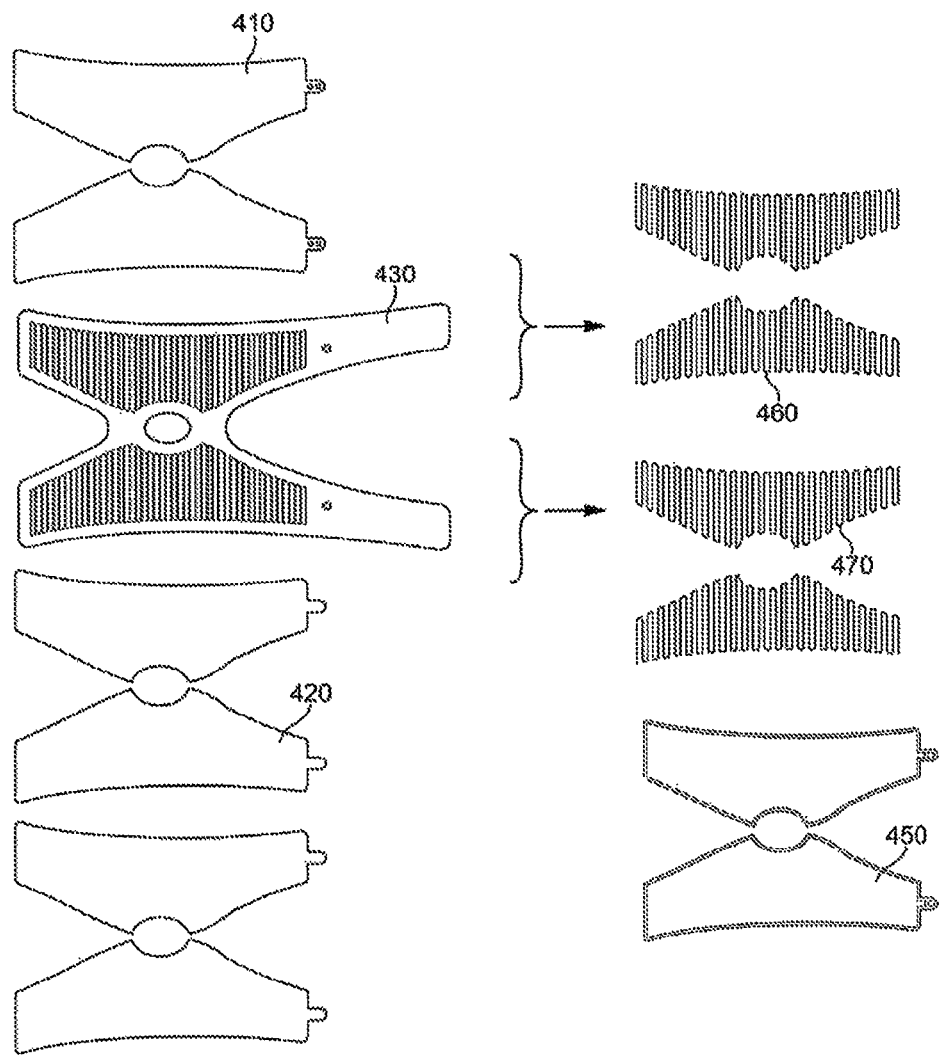
FIG. 14 shows the separate layers of the knee applicator of FIG. 13 on the left hand side and, on the right hand side, the joining patterns used to join together the various layers of the applicator of FIGS. 13 and 14.

Cold layer 410 and hot layer 420 are also joined, for example by welding, to opposite sides of intermediate layer 430 to define a pattern of flow channels. As shown in FIG. 14, weld line 460 joins cold layer 410 to intermediate layer 430 and weld line 470 joins hot layer 420 to intermediate layer 430. This provides a continuous and meandering planar flow path between each of the cold and hot layers and the intermediate layer. Cold and hot layers 410 and 420 are welded to intermediate layer 430 in such a position that the flow paths overlie the holes 440 in the intermediate layer. This provides a three-dimensional flow path for the thermal energy transfer fluid which pass through the intermediate layer.

Figure 15A:
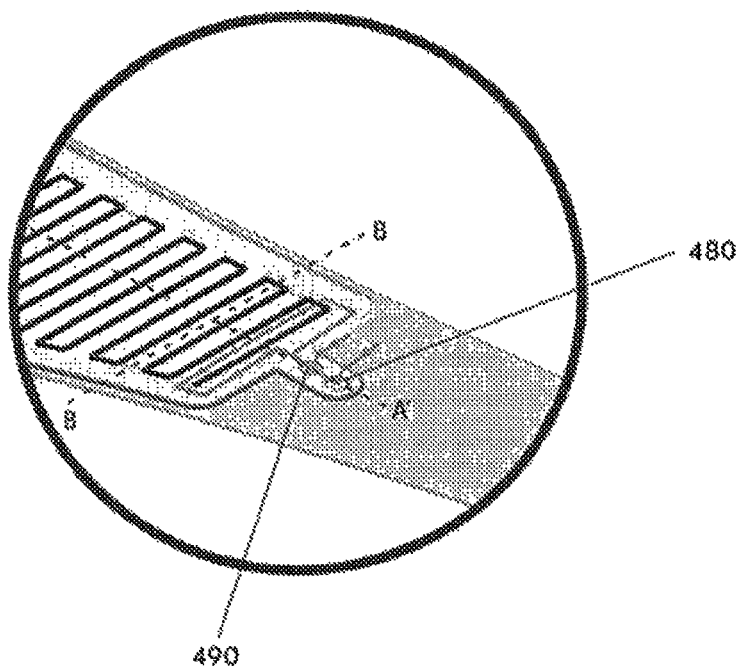
FIG. 15a is an enlarged view of a portion of the knee applicator of FIG. 13 including an inlet and an outlet for a thermal energy transfer fluid.
Figure 15B:
Figure 15B:
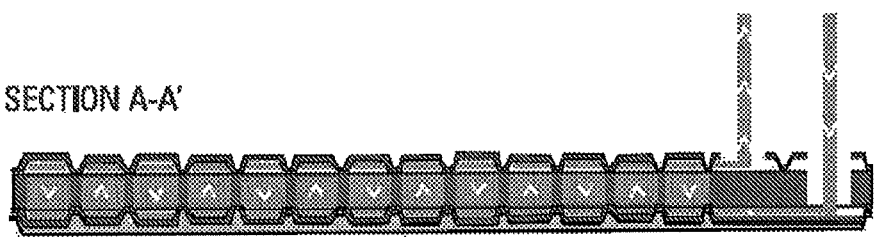
Figure 15C:

As shown generally in FIGS. 15a, 15b and 15c, thermal energy transfer fluid flows under pressure from an inlet 480 into the flow path defined between cold layer 410 and intermediate layer 430, through holes 440 in intermediate layer 430 and into the flow path defined between hot layer 420 and intermediate layer 430. The fluid can also pass back through downstream holes in the intermediate layer and return to the flow path defined between cold layer 410 and intermediate layer 430. Thermal energy transfer fluid leaves the applicator through outlet 490 to return to reservoir 80.

In operation, circulation pump 70 pumps thermal energy transfer fluid from reservoir 80 at a relatively higher temperature to inlet 200 of lower casing section 110. The thermal energy transfer fluid passes along the continuous flow path provided by channels 180 in lower casing section 110 and is expelled from outlet 210 having been cooled to a lower temperature by lower plate 160 maintained at a relatively lower temperature. The polarity of the direct current applied to plates 160,170 can be controlled and varied by the operator as required using the controller of monitoring and control system 50 to change the temperature of lower plate 160 and therefore change the temperature of the thermal energy transfer fluid leaving outlet 210.

The irregular shaped and/or irregularly positioned projections 130 disturb the flow of the thermal energy transfer fluid as it flows along the continuous flow path provided by channels 180. This induces turbulent flow of the thermal energy transfer fluid which excites the thermal energy transfer fluid molecules and forces the molecules to collide with one another. The collisions generate and radiate additional thermal energy which is absorbed by the relatively lower temperature casing of thermal energy source 90. Cooling fan 170 circulates air past fins 160 and radiates heat to the surrounding cooler air. Cooling source 90 provides for rapid and controllable transfer of thermal energy from the lower temperature plate 160 of the cooling source 90 to the higher temperature thermal energy transfer fluid entering at inlet 200.

With reference to the embodiment of applicator 60 shown in FIGS. 11 and 12 and constructed from a number of discrete thermal energy transfer portions 300, thermal energy transfer fluid leaving cooling source 90 at a relatively colder temperature is pumped under pressure by pump 70 along a flow line (not shown) to an inlet of applicator 60. Thermal energy transfer fluid then flows though flow pipes 335 to an inlet of each of discrete portions 300 and into cold fluid circuit 340. The fluid passes through cold fluid circuit 340 and along the network of flow tubes into hot fluid circuit 350. As the thermal energy transfer fluid at a relatively lower temperature flows through flow tubes 320, the body surface in contact with the discrete portions 300 is cooled and thermal energy is carried by the fluid away from the treatment area. Thermal energy transfer fluid leaving the hot fluid circuit at a relatively higher temperature then passes back along flow pipes 335 and is returned to reservoir 80 through a return line (not shown).

With reference to the knee applicator 400 shown in FIGS. 13 to 15c, thermal energy transfer fluid is pumped by pump 70 along a flow line (not shown) to applicator inlet 480 at a relatively lower temperature and circulates through the three-dimensional flow path defined by the weld pattern between cold layer 410 and intermediate layer 430 and between hot layer 420 and intermediate layer 430. Thermal energy transfer fluid is distributed substantially across the total area of each of the pair of sealed pouches formed between hot and cold layers 410,420 to maximise the thermal energy transfer between applicator 400 and the treatment area. The complex three-dimensional flow path through holes 440 in intermediate layer 430 disturbs the flow of thermal energy transfer fluid thereby releasing additional thermal energy and improving the efficiency of thermal energy transfer between the thermal energy transfer fluid and the treatment area. Thermal energy transfer fluid leaving applicator outlet 490 at a relatively higher temperature is then returned via a return line (not shown) to reservoir 80.

Whether thermotherapy system 10 is coupled to applicator 60 or knee applicator 400, the temperature of the thermal energy transfer fluid entering the applicator is monitored and controlled by a microprocessor in the controller of monitoring and control circuit 50. The microprocessor receives temperature data from sensors positioned at either side of interface layer 240 and from the cooling fluid inlet and outlet of the applicator. The temperature data enables the microprocessor to adjust the operating parameters of the cooling system 40 to vary the temperature of the thermal energy transfer fluid and therefore the temperature at treatment site. The microprocessor can make adjustments to one or more of the temperature of the thermal energy transfer fluid leaving the cooling source, the circulating pump pressure, the thermal energy transfer fluid flow rate past projections 130 of heat sink 120 and the rate of air circulation at the cooling source effected by cooling fan 170 to affect the temperature at the treatment site.

The foregoing description relates to the construction and operation of a basic thermotherapy system 10 which can be used with an applicator 60 or a knee applicator 400 to administer thermotherapy. The inventor has also appreciated that a key factor in improving the efficiency of thermal energy transfer between an applicator and a treatment site is the ability to control accurately and manipulate the behaviour of the molecules that make up the interface between the applicator and the treatment site as well as the molecules of the thermal energy transfer fluid. The inventor has appreciated that known apparatuses for the application of thermotherapy do not provide for such active control and manipulation of molecule behaviour and as such, they are incapable of optimising the application of thermotherapy.

An alternative thermotherapy system 600 (see FIG. 17) has therefore also been developed which uses a modulated high frequency electric current to manipulate the behaviour of the molecules of the thermal energy transfer fluid and the interface material. This system shall now be described in detail.

Figure 16:
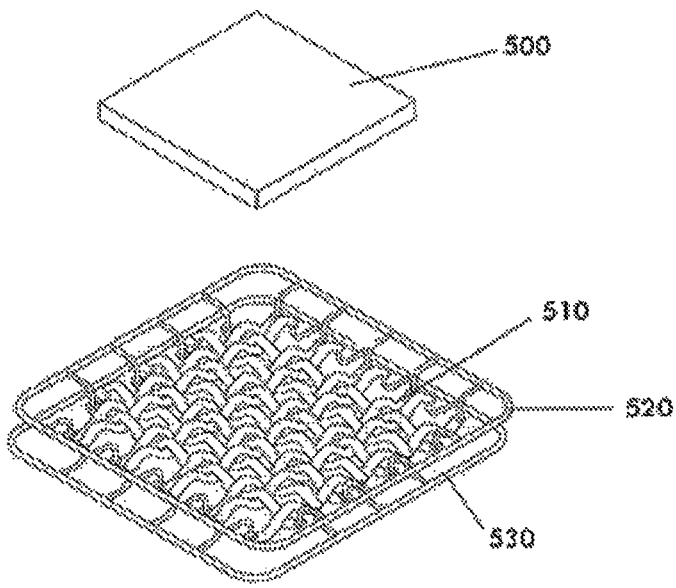
FIG. 16 is an exploded view of a composite interface layer and electrically conductive supporting layer.
Figure 17:
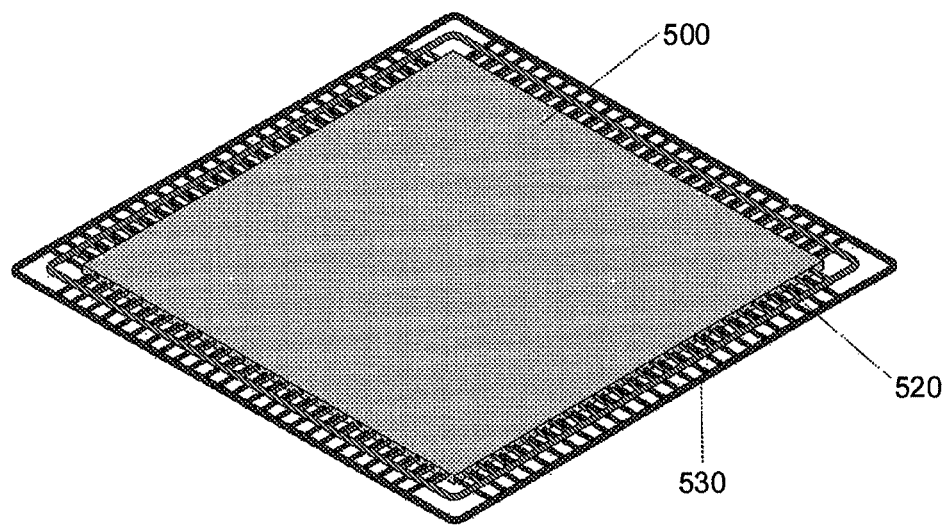
FIG. 17 is an enlarged view of the composite interface layer and electrically conductive supporting layer of FIG. 16.
Figure 18:
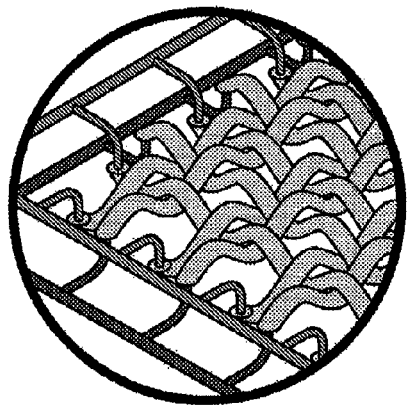
FIG. 18 is a further enlarged view of the composite interface layer and electrically conductive supporting layer of FIGS. 16 and 17 showing primary and secondary circuits attached to the electrically conductive supporting layer.

As shown generally in FIGS. 16 to 18, an electrically conductive supporting mesh layer 510 woven from metallic strands supports an interface layer 500. Preferably, supporting layer 510 is located within interface layer 500 at an intermediate position. Metallic mesh layer 510 provides support for flexible, gel-like interface layer 500 and provides an electrically conductive medium through interface material 500. A thin, electrically conductive sheet full of holes may alternatively be used as supporting layer 510, however a woven construction is advantageous as it offers improved flexibility and conformability of interface layer 500.

Preferably the weave is an open weave. More preferably, the weave is in the range of approximately 5% to 25% material area to % 95 to % 75 interstitial or open area. However, the weave may be modified to alter the conductive properties of the supporting layer and may be closer in some areas than in others as discussed further below.

Preferably supporting layer 510 is made of a fine wire of maraging steel, the wire having a Nickel content of approximately 10% to 25%. More preferably the wire has a Nickel content of approximately 15% to 20%.

Thermistors are attached to metallic supporting layer 510 which measure the temperature of interface layer 500 substantially across the entire treatment site. A primary circuit 520 is connected to the supporting layer to relay temperature data from the thermistors to be relayed to a controller, as described further below. A secondary, driving circuit 530 is separately connected to supporting layer 510 and enables a modulated high frequency electric current to be applied through mesh layer 510 to affect the behaviour of the molecules of interface layer 500 as discussed further below.

Figure 19:
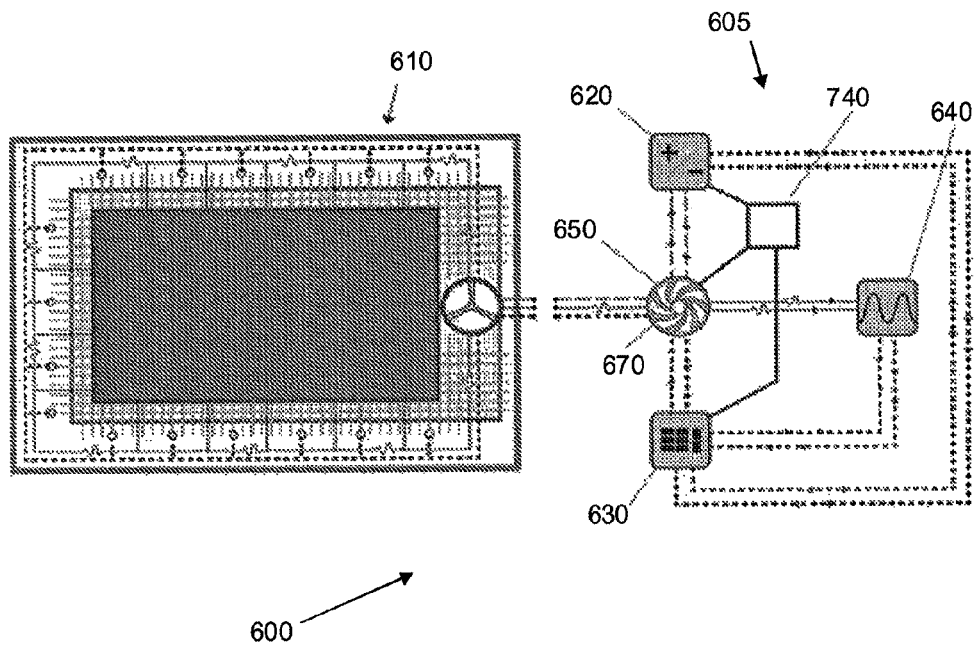
FIG. 19 is a schematic view of a control system for connection to an applicator.
Figure 20:
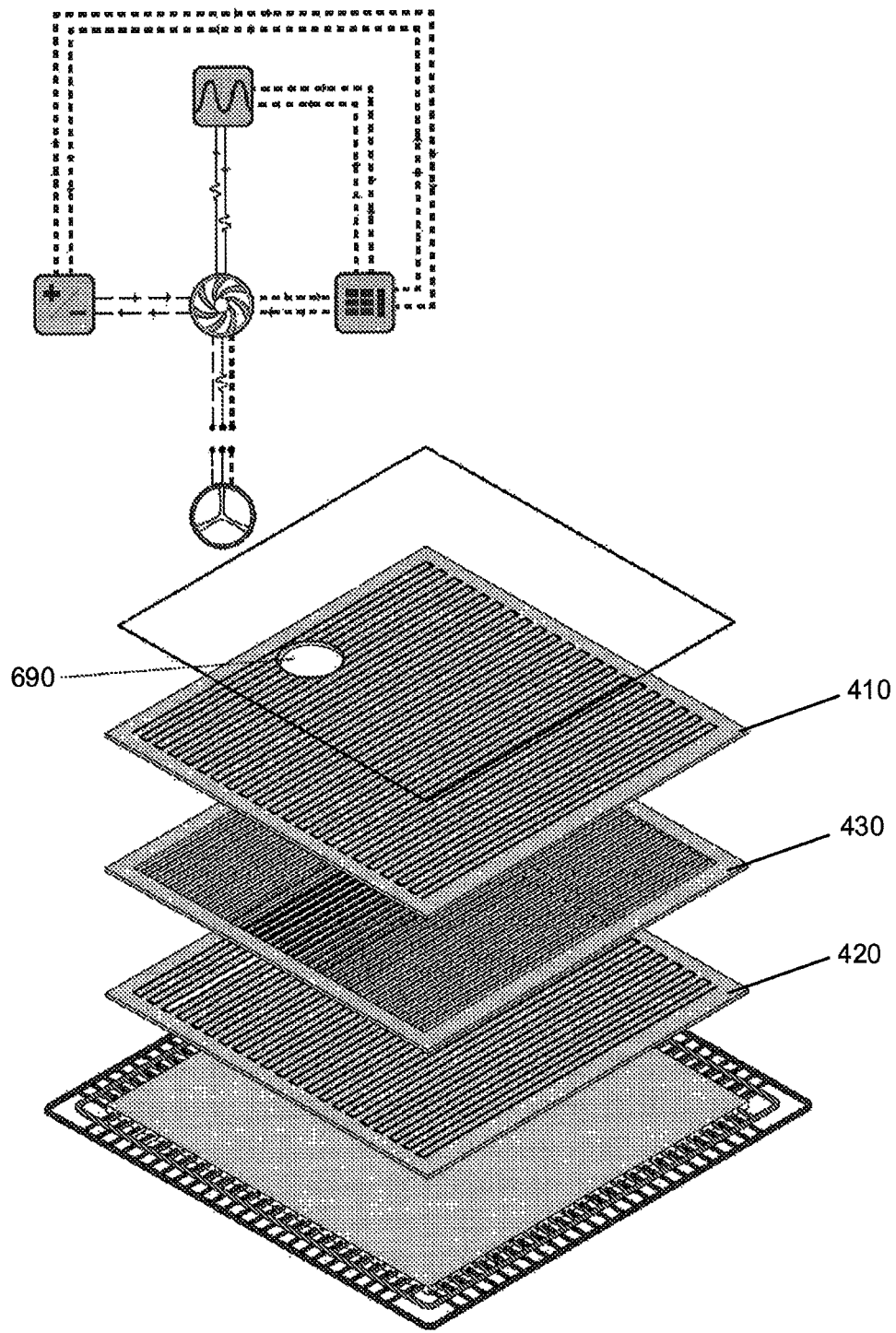
FIG. 20 is an exploded view of the control system of FIG. 19 and the applicator.

A monitoring and control system 605 is provided for connection to a suitable applicator 610 as shown in FIGS. 19 and 20. Applicator 610 has the same layered construction as knee applicator 400 though may be used for applying treatment to an alternative part of the body. Control system 605 includes power source 620 which may be one of a number of known power sources such as a fuel cell for providing a supply of current to energise the electrically conductive supporting layer 510. Control system 605 also includes a controller 630 for controlling the various components of the system, an oscillator 640 for producing a modulated high frequency current and a valve unit 650 for connecting control system 605 to applicator 610 and controlling the flow of thermal energy transfer fluid through applicator 610. Controller 630 is connected to power source 620, oscillator 640 and valve unit 650. Valve unit 650 is also connected to oscillator 640 and power source 620.

Valve unit 650 and oscillator 640 form a phase change pump. The phase change pump has two main functions as described below. The first is to agitate thermal energy transfer fluid circulating through the applicator 610 to cool the fluid by convection cooling. The second function is to change the phase of the interface material forming the highly conductive interface between the applicator 610 and the treatment site in an alternative embodiment described below.

Figure 21:
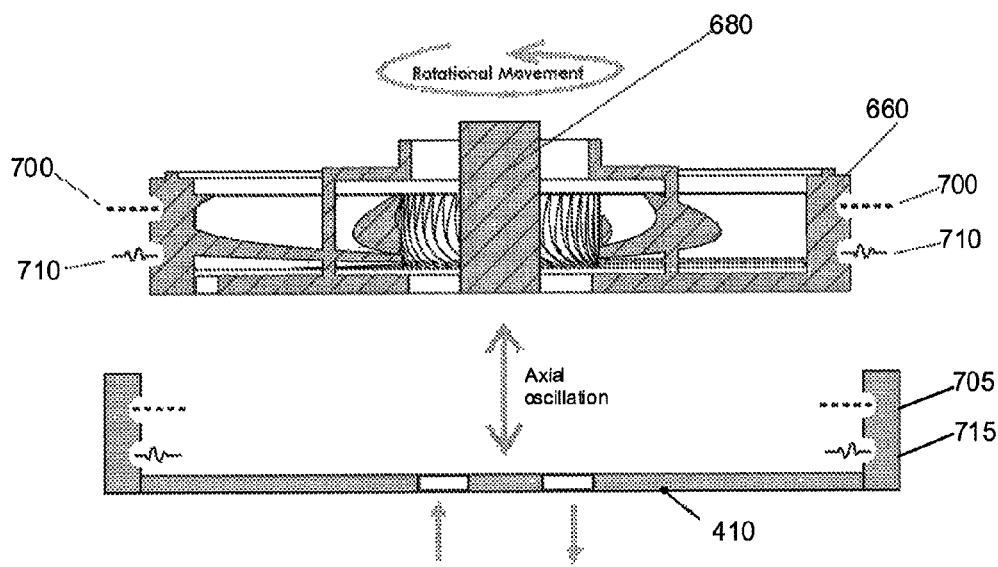
FIG. 21 shows a valve unit for connecting the control system of FIGS. 19 and 20 to an applicator.
Figure 22:
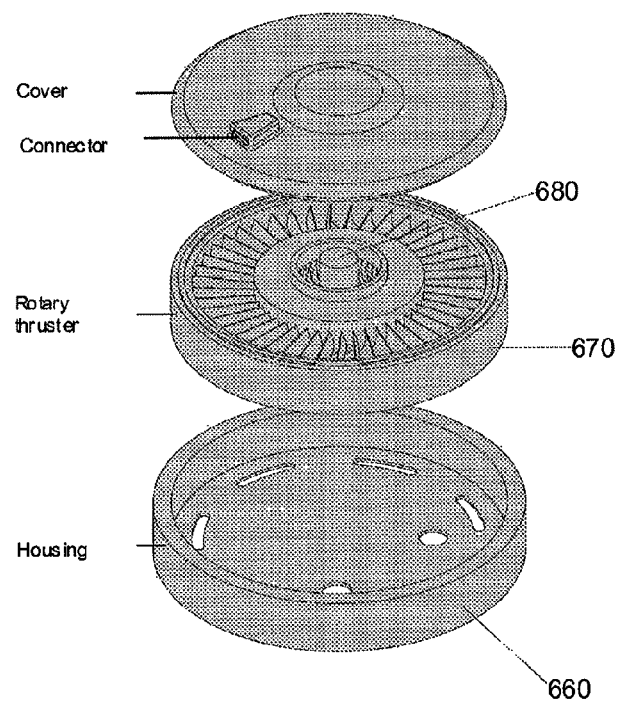
FIG. 22 is an exploded view of the valve unit of FIG. 21.
Figure 23:
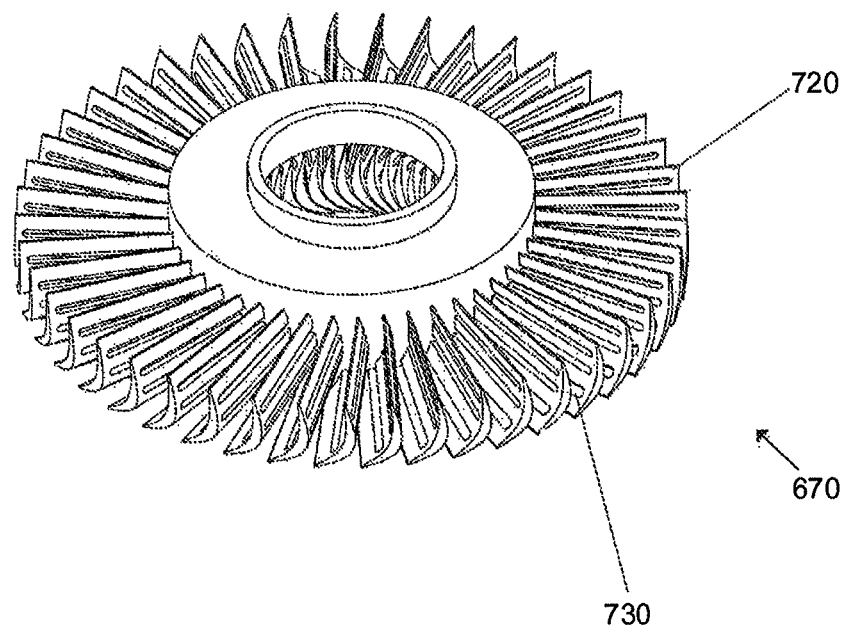
FIG. 23 is a perspective view of a rotary thruster of the valve unit of FIGS. 21 and 22.
Figure 24:
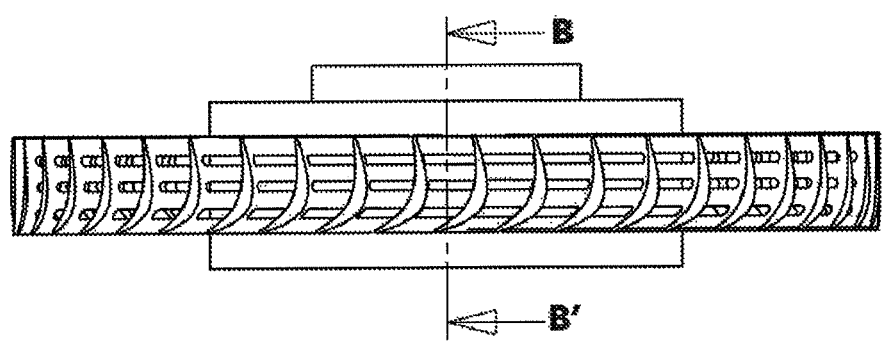
FIG. 24 is a side view of the rotary thruster of FIG. 23.
Figure 25:
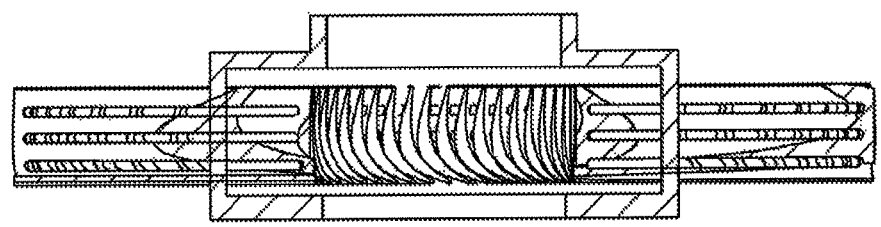
FIG. 25 is a section view along line B-B of the rotary thruster of FIG. 24.

Valve unit 650, shown in detail in FIGS. 21 and 22, includes a housing 660 for housing an agitator 670 shown in more detail in FIGS. 23 to 25. The agitator is for agitating and inducing turbulent flow of thermal energy transfer fluid passing through the valve unit 650 in order to cool the thermal energy transfer fluid. The agitator is preferably a rotary thruster. Preferably, the rotary thruster comprise a variably rotating disc of three dimensional profile having attachable blades or vanes or integrally formed with blades or vanes, such as a turbine, impeller or propeller.

The rotary thruster is driven by a magnetic drive coupling 680. Magnetic drive coupling 680 rotates the rotary thruster 670 and also permits axial oscillation of the rotary thruster in response to a modulated high frequency signal generated by oscillator 640. A combination of rotation and transitory movement of the rotary thruster, such as for example, axial oscillation, agitates the thermal energy transfer fluid flowing past the rotary thruster in order to cool the fluid.

Valve unit 650 is connected by a snap-fit or other quick release type connection to a correspondingly shaped connector 690 (see FIG. 20) in applicator 610. When valve unit 650 is connected to applicator 610, connections 700 connect valve unit 650 to corresponding connections 705 of primary, measuring circuit 520. This enables temperature measurement data to be relayed from thermistors attached to the electrically conductive supporting layer 510 to be relayed to the controller 630. Connections 715 also connect valve unit housing 660 to secondary, driving circuit 530 separately connected to metallic mesh weave 510. This enables a high frequency modulated signal generated by oscillator 640 to be passed through electrically conductive supporting layer 510.

When valve unit 660 is connected to connector 690 of applicator 610, thermal energy transfer fluid is circulated by rotary thruster 670 from the flow path defined between the hot layer 410 and intermediate layer 430, through valve unit 660 and back into the flow path defined between cold layer 410 and intermediate layer 430. The controller 630 may be programmed to operate rotary thruster 670 either continuously or for discrete periods of time in order to vary the temperature of the thermal energy transfer fluid in applicator 610.

As shown in FIG. 23, rotary thruster 670 has a plurality of vanes 720, each vane comprising one or more apertures 730 shown by way of example only in FIG. 23 as slots. Apertures of other shapes such as circular holes, or protrusions from the vanes may be used to provide the same result as discussed further below. As the thermal energy transfer fluid is circulated past rotary thruster 670 as it rotates and oscillates axially, a portion of the thermal energy transfer fluid is forced through apertures 730 which further agitates the fluid and increases the convection cooling effect of the phase change pump.

In operation, the rotary thruster 670 of the phase change pump circulates thermal energy transfer fluid through applicator 610. A modulated high frequency signal is applied by oscillator to magnetic drive coupling 660 causing rotary thruster 670 to oscillate axially relative to valve unit housing 660. As thermal energy transfer fluid is forced through valve unit 660 by vanes 720, a portion of the fluid is forced through apertures 730. This agitates and disturbs the thermal energy transfer fluid to produce turbulent flow and creates micro-bubbles in the thermal energy transfer fluid. The micro-bubbles expand and eventually collapse. This build up and collapse of micro-bubbles has been found to release thermal energy from the thermal energy transfer fluid and therefore reduce temperature of the thermal energy transfer fluid by convection cooling.

Oscillator 640 coupled to controller 630 also passes a modulated high frequency electrical signal which may also have varying amplitude through secondary, driving circuit 530 to electrically conductive supporting layer 510. The modulated high frequency signal excites the molecules of interface layer 500 which enhances the ability of the interface layer to make contact at the molecular level with the patient's skin at the treatment area. This increases the rate of thermal energy transfer between the thermal energy transfer fluid and the treatment area. The current applied to electrically conductive supporting layer 510 also causes the supporting layer to vibrate which further excites the molecules of the interface layer 500 and enhances the transfer of thermal energy between the interface layer and the treatment site.

The frequency and amplitude of the signal produced by oscillator 640 may be adjusted as required by the operator at a user interface of controller 630 or may be varied according to pre-programmed treatment profiles.

The effect of the modulated high frequency signal being applied to both rotary thruster 670 and directly to interface layer 500 is that the thermal energy penetrates deeper into the tissue at the treatment site improving the effects of the Cryotherapy treatment. The thermotherapy system can therefore be accurately controlled to maintain an environment best suited for the treatment of a particular injury or condition.

A number of variations to thermotherapy system 600 previously described in relation to FIGS. 17 to 25 have also been developed and shall now be described.

A number of valve units 650 may be connected to control system 605 allowing identical or different shaped applicators 610 to be connected to each of the valve units 650. This allows the system to be used to administer thermotherapy to two or more parts of the patient's body simultaneously.

The oscillator 640 and the rotary thruster 670 may optionally be located remotely from valve unit 650, in which case a pipe (not shown) for thermal energy transfer fluid would connect the phase change pump to applicator 610.

A thermotherapy system might also include the phase change pump in addition to thermal energy transfer fluid recirculation system 30 and cooling system 40 of thermotherapy system 10. In such a system, the phase change pump would be used to agitate a continual flow of thermal energy transfer fluid entering applicator 610 through valve unit 660 from reservoir 80 and thereby provide additional cooling of the thermal energy transfer fluid.

Electrically conductive supporting layer 510 might be constructed from a shape memory alloy so that when a driving current is passed by secondary circuit 530 from a source of current to energise the electrically conductive supporting layer 510 it changes shape and constricts applicator 610 around the treatment site, ensuring that it conforms more closely the contours of the particular body part.

In an alternative embodiment, an interface layer for use with an applicator 60, 400 or 610 is a colloid contained within a membranous enclosure through which a supporting layer is positioned to support the membranous enclosure and enable it to be joined to an outside surface of applicator 610. In an inactivated form, the colloid is in a liquid state comprising electrically conductive particles supported in suspension. When an electric current is passed to the membranous enclosure through an electrically conductive supporting layer by secondary, driving circuit 530, or another suitable supply means, the colloid is activated so that it becomes a more viscous and gel-like highly conductive layer with similar thermal energy transfer properties to an interface layer 240 or 500 described above.

In a further alternative embodiment, or in conjunction with any of the aforementioned embodiments, an ultrasound generator 740 is included in the control system 50 or 605 (see, for example, FIG. 19). In operation, an ultrasound signal is passed from the ultrasound generator to the interface material layer 240 or 500 through the supporting layer 250 or 510 or via an alternative connection to the interface layer. An ultrasound signal is then applied continuously or in discrete bursts to the interface layer in order to excite the molecules of the interface material and enhance the thermal conductivity of the interface layer.

In this, or a further alternative embodiment, interface layer 500 in an inactivated form is a colloid comprising a compound in suspension and is contained within a membranous enclosure supported by a supporting layer that is welded or otherwise attached to an outer surface of applicator 610. In operation, the interface layer material is activated by a short burst of ultrasound generated by ultrasound generator 740 and becomes more viscous and gel-like. The ultrasound signal changes the state of the interface material from a transparent liquid in which the dimer molecules from which the compound is formed are bent and self-locked by aromatic stacking interactions, to an opaque gel in which the conformation is planar with interlocked aggregates provides a highly conductive layer with similar properties to the interface layer 240 or 500.

The invention claimed is:

1. An applicator for applying thermotherapy to a part of the human or animal body comprising:
    a flexible enclosure in which thermal energy transfer fluid can circulate;
    a connector for connecting the applicator to a control system;
    an interface layer attached to an outer surface of the flexible enclosure for providing a thermally conductive interface between the flexible enclosure and a part of a human or animal body; and
    an electrically conductive supporting layer positioned within the interface layer for supporting the interface layer and retaining the interface layer against the flexible enclosure;
    wherein the electrically conductive supporting layer is adapted to receive an electrical signal from the control system; and
    wherein the interface layer is a colloid including electrically conductive particles in suspension and held within a membranous enclosure supported by the electrically conductive supporting layer, and the colloid is activatable in response to an electric current to become more viscous and gel-like.

2. An applicator according to claim 1 having a primary, measurement circuit which connects the electrically conductive supporting layer to the connector so that data can be passed from the electrically conductive supporting layer to the control system.

3. An applicator according to claim 1 having a secondary, driving circuit which connects the electrically conductive supporting layer to the connector so that an electric current may be passed to the electrically conductive supporting layer from the control system.

4. An applicator according to claim 1 including an intermediate layer through the flexible enclosure, having a plurality of holes to permit the flow of thermal energy transfer fluid from one side of the intermediate layer to the other.

5. An applicator according to claim 1 including a network of flow tubes positioned within the flexible enclosure for directing the flow of a thermal energy transfer fluid through the enclosure.

6. An applicator according to claim 5 wherein the electrically conductive supporting layer is joined to the flexible enclosure adjacent an edge of the interface layer.

7. An applicator according to claim 5 wherein the flexible enclosure and electrically conductive supporting layer are joined by welding.

8. An applicator according to claim 1 wherein the connector is a snap fit or other quick-release type connector.

9. An applicator according to claim 1 wherein in operation, the electrically conductive supporting layer is energised by a control system to excite the molecules of the interface layer and increase the thermal conductivity of the interface layer.

10. An applicator according to claim 1 wherein the interface layer is an elastomer made of a Silicon based gel loaded with particles of Boron Nitride.

11. An applicator according to claim 10 wherein the ratio of Silicon based gel to Boron Nitride particles is in the range of approximately 0.5 to 0.8 Silicon to the range of approximately 0.5 to 0.2 Boron Nitride particles.

12. An applicator according to claim 1 wherein the interface layer is activatable in response to an ultrasound signal received from the control system to become more thermally conductive.

13. An applicator according to claim 1 wherein the interface layer is a colloid held within a membranous enclosure and activatable in response to an ultrasound signal received from the control system to become more viscous and gel-like.

14. An applicator according to claim 1 wherein the supporting layer is a woven mesh of an electrically conductive material.

15. An applicator according to claim 14 wherein the supporting layer is made of a fine wire of maraging steel with a Nickel content of approximately 10% to 25%.

16. An applicator according to claim 14 wherein the weave is a substantially open weave.

17. An applicator according to claim 1 generally shaped to conform to a particular part of the human or animal body.

18. An applicator according to claim 1 including a constrictor for constricting the applicator so that it conforms more closely to a particular part of a human or animal body.

19. An applicator according to claim 1 wherein a thermal energy transfer fluid suitable for circulation through the enclosure is a non-aqueous fluorocarbon based fluid.

20. An applicator according to claim 1 further including a valve unit for connecting the applicator to a control system, the valve unit comprising:
   a housing to be received within the connector of the applicator; and
   an agitating body moveably coupled to the housing for imparting movement to the thermal energy transfer fluid in the enclosure.

21. A valve unit according to claim 20 wherein the agitating body is a rotary thruster.

22. A valve unit according to claim 21 wherein the agitating body has a plurality of vanes for imparting movement to the thermal energy transfer fluid.

23. A valve unit according to claim 22 wherein the vanes have apertures which allow thermal energy transfer fluid to pass from one side of each vane to the other as the rotary thruster imparts movement of a thermal energy transfer fluid through the flexible enclosure.

24. An applicator according to claim 1 further including a heat exchanger for varying the thermal energy of a thermal energy transfer fluid to be circulated through the applicator, the heat exchanger comprising:
   a casing defining a flow path for a thermal energy transfer fluid; and
   a heat sink having a plurality of irregularly positioned and/or irregularly shaped projections which extend into the flow path for the thermal energy transfer fluid; wherein in use, the irregularly positioned and/or irregularly shaped projections disturb the flow of the thermal energy transfer fluid through the flow path to create turbulent, non-laminar fluid flow.

25. A heat exchanger according to claim 24 further including a thermal energy source coupled to the heat sink for varying the temperature of the thermal energy transfer fluid flowing along the fluid flow path past the projections of the heat sink.

26. An applicator according to claim 1 further including a control system comprising:
   a control system connector for connecting the control system to the applicator connector;
   an electrical current source for energizing the electrically conductive supporting layer; and
   a controller for controlling the properties of current flowing from the current source.

27. A control system according to claim 26 wherein the controller includes an oscillator for supplying a modulated current source to the electrically responsive supporting layer.

28. A control system according to claim 26 including an ultrasound generator controlled by the controller for supplying an ultrasound signal to the interface layer of the applicator to change the state of the interface material and cause it to become more viscous and gel-like.

29. An applicator according to claim 2 having a secondary, driving circuit which connects the electrically conductive supporting layer to the connector so that an electric current may be passed to the electrically conductive supporting layer from the control system.

* * * * *